United States Patent
Sass et al.

(10) Patent No.: US 9,827,105 B2
(45) Date of Patent: Nov. 28, 2017

(54) ENDOPROSTHESIS FOR KNEE ARTHRODESIS

(71) Applicant: IMPLANTCAST GMBH, Buxtehude (DE)

(72) Inventors: Jens Sass, Buxtehude (DE); Georg Gosheger, Münster (DE); Martin Wensing, Havixbeck (DE); Sebastian Borgert, Coesfeld (DE); Axel Zscheile, Altenberge (DE)

(73) Assignee: IMPLANTCAST GMBH, Buxtehude (DE)

( * ) Notice: Subject to any disclaimer, the term of this patent is extended or adjusted under 35 U.S.C. 154(b) by 51 days.

(21) Appl. No.: 15/044,524

(22) Filed: Feb. 16, 2016

(65) Prior Publication Data
US 2016/0242917 A1    Aug. 25, 2016

(30) Foreign Application Priority Data
Feb. 19, 2015  (DE) .................. 10 2015 102 391

(51) Int. Cl.
*A61F 2/38* (2006.01)
*A61F 2/30* (2006.01)

(52) U.S. Cl.
CPC ............ *A61F 2/3845* (2013.01); *A61F 2/389* (2013.01); *A61F 2/3859* (2013.01); *A61F 2002/30492* (2013.01); *A61F 2002/30607* (2013.01); *A61F 2002/30622* (2013.01)

(58) Field of Classification Search
CPC .............................. A61F 2/384; A61F 2/3845
See application file for complete search history.

(56) References Cited

U.S. PATENT DOCUMENTS

| 3,765,033 | A | * | 10/1973 | Goldberg | ............... A61F 2/384 623/20.26 |
| 2014/0025172 | A1 | * | 1/2014 | Lucas | .................... A61F 2/384 623/18.12 |
| 2014/0025174 | A1 | | 1/2014 | Lucas et al. | |

FOREIGN PATENT DOCUMENTS

WO    2010/025704    3/2010

* cited by examiner

*Primary Examiner* — Thomas J Sweet
*Assistant Examiner* — Megan Wolf
(74) *Attorney, Agent, or Firm* — Sand & Sebolt

(57) ABSTRACT

An endoprosthesis for knee joint arthrodesis having a femur portion including a femur attachment structure; a tibia portion including a tibia attachment structure; a coupling section formed on the femur portion and a coupling section formed on the tibia portion. The coupling sections are pivotably connected to one another about a prosthesis pivot axis that extends in the installed position of the endoprosthesis horizontally from medial to lateral. A locking element is moveable between locking and release positions. In the locking position the locking element rigidly locks the coupling sections in a predefinable pivot position. In the release position the coupling sections are pivotable relative to one another about the prosthesis pivot axis. A retaining and return means and an unlocking mechanism are provided. The retaining means forces the locking element into the locking position. The unlocking mechanism moves the locking element into the release position.

12 Claims, 6 Drawing Sheets

ENDOPROSTHESIS FOR KNEE ARTHRODESIS

The invention relates to an endoprosthesis for knee joint arthrodesis.

Knee joint arthrodesis, i.e., the operative stiffening of the knee joint with a metallic implant, an endoprosthesis, is regularly carried out, for example, after multiple failures of a knee joint endoprosthesis, in the case of a bone tumor, in the case of bone infections, in the case of a trauma and in the case of neurological diseases, such as poliomyelitis, the so-called infantile paralysis.

In the past, different metallic implants were used for such purpose, which ensured a complete stiffening of the knee joint and fixation of the upper leg to the lower leg at the position of the original knee joint at a predefined and fixed angle. Previous systems, such as that according WO 2010/025704 A1, are generally comprised of shaft systems, which are anchored in the remaining shin and thigh bones (tibia and femur) and then fixed with coupling sleeves, i.e., fully, permanently stiffened. Common to all previously known approaches is the fact that the functional results of the procedure using this approach are very poor due to the permanent stiffening of the knee joint at a predefined angle.

The freedom of movement of an affected patient having a knee joint permanently stiffened at a fixed angle is generally severely limited. Thus, it is possible, in particular, only with great difficulty to transport an affected patient having a previously known implant in transportation means, such as airplanes, autos or the like. Moreover, sexual activity is also shown to be severely restricted given the lack of flexibility of the knee. In addition, secondary arthrotic changes in the region of the lower lumbar spine and the hip and ankle joints are not uncommon due to the transfer of force to the surrounding joints.

The invention is intended to remedy this by creating an endoprosthesis for knee joint arthrodesis, which on the one hand guarantees the desired and stable stiffening, thus in particular during walking, resulting in a stable control of the stiffened leg when extended, but on the other hand permits a change in the flexed position of the lower leg relative to the upper leg.

This object is achieved according to the present invention with an endoprosthesis for knee joint arthrodesis having a femur portion which includes a femur attachment structure for the fixed connection to the distal end of the femur, a tibia portion which includes a tibia attachment structure for the fixed connection to the proximal end of the tibia, a coupling section on the femur side formed on the femur portion, a coupling section on the tibia side formed on the tibia portion, wherein the coupling section on the femur side and the coupling section on the tibia side are pivotally connected relative to one another about a prosthesis pivot axis, which extends in the installed position of the endoprosthesis as the knee replacement, essentially horizontally from medial to lateral and, thus, corresponds in its position essentially to the position of the pivot axis of the natural knee, at least one locking element which is moveable back and forth between a locking position in which it rigidly locks the coupling section on the femur side and the coupling section on the tibia side in a predefinable pivot position, and a release position, in which a pivoting of the coupling section on the femur side and the coupling section on the tibia side relative to one another about the prosthesis pivot axis is enabled. a retaining and return means, which forces the locking element into the locking position with the aid of a holding force and holds it in said position, and an unlocking mechanism, by means of which the locking element may be displaced against the holding force from the locking position to the release position. Advantageous refinements of the endoprosthesis according to the invention are that the locking element, as part of the unlocking mechanism, has a magnetic element, to which a force may be applied with a magnet moved from the outside into proximity with this magnetic element, by means of which the locking element is displaceable against the holding force from the locking position to the release position. The endoprosthesis is further characterized in that one of the coupling sections, the coupling section on the femur side or the coupling section on the tibia side, includes a hollow cylindrical section having a circular cross section sealed at both end faces, the cylinder longitudinal axis of which is oriented along the prosthesis pivot axis, and that the other coupling section, the coupling section on the tibia side or the coupling section on the femur side, also includes a chamfered bearing section extending parallel to the prosthesis pivot axis for rotatable mounting of the hollow cylindrical section about the cylinder longitudinal axis, and a stop wall extending transversely to the prosthesis pivot axis, which forms a stop on the end face for the hollow cylindrical section, wherein at least two receiving holes oriented in parallel to the prosthesis pivot axis are provided at different positions in the stop wall, wherein the locking element comprises a piston plate disposed in an interior space of the hollow cylindrical section displaceable in the longitudinal direction of the cylinder, on which at least one locking pin, projecting from said piston plate in the direction of the stop wall, extending in the longitudinal direction of the cylinder, is eccentrically disposed, wherein the free end of locking pin penetrates an opening in the end face of the hollow cylindrical section facing the stop wall and, in a relative pivot position of the two coupling sections, in which it rests flush with one of the receiving holes in the stop wall, is able to extend into or retract from said opening by a movement of the piston plate in the longitudinal direction of the cylinder. The endoprosthesis is further characterized in that multiple, in particular, four, uniformly and eccentrically disposed locking pins extending in the longitudinal direction of the cylinder are fixed on the piston plate, that these correspondingly positioned openings penetrate the end face of the hollow cylindrical section facing the stop wall, and that receiving holes are provided in the stop wall in the number corresponding to the number of locking pins and in an arrangement corresponding to the arrangement of the locking pins. Furthermore, the piston plate includes or forms the magnetic element. The piston plate includes at least one recess projecting inward from its edge, and that a rib adapted in cross section to the shape of the recess, projecting into the interior space and extending in the longitudinal direction of the cylinder, is provided on a wall delimiting the interior space of the hollow cylindrical section, which rib engages in the recess for a rotationally-resistant and tilt-resistant guidance of the piston plate. At least the free end of the locking pin is formed from a magnetizable or from a magnetic material, and that a retaining magnet, which forms the retaining and return means, is disposed in each of the receiving holes. The hollow cylindrical section is disposed on the coupling section on the femur side, the bearing section on the coupling section on the tibia side. The two coupling sections are rotationally connected relative to one another about the prosthesis pivot axis by means of a pivot- and threaded bolt guided along the prosthesis pivot axis. The endoprosthesis is further characterized by pivot angle limiting structures on the interacting coupling sections, which limit a relative pivoting of tibia portion and femur portion with respect to a predefined pivot angle. The femur attachment structure is a femur shaft. The tibia attachment structure is a tibia shaft.

According to the invention, the novel endoprosthesis for knee joint arthrodesis has the following components:
a. a femur portion, which includes a femur attachment structure for the fixed connection to the distal end of the femur (thigh bone),
b. a tibia portion, which includes a tibia attachment structure for the fixed connection to the proximal end of the tibia (shin bone),
c. a coupling section on the femur side formed on the femur portion,
d. a coupling section on the tibia side formed on the tibia portion, wherein the coupling section on the femur side and the coupling section on the tibia side are pivotably connected relative to one another about a prosthesis pivot axis, which extends in the installed position of the endoprosthesis, as the knee replacement, essentially horizontally from medial to lateral and, thus, corresponds in its position essentially to the position of the pivot axis of the natural knee,
e. at least one locking element, which is moveable back and forth between a locking position, in which it rigidly locks the coupling section on the femur side and the coupling section on the tibia side in a predefinable pivot position, and a release position, in which a pivoting of the coupling section on the femur side and the coupling section on the tibia side relative to one another about the prosthesis pivot axis is enabled.
f. a retaining and return means, which forces the locking element into the locking position with the aid of a holding force and holds it in the said position, and
g. a release mechanism, by means of which the locking element may be displaced against the holding force from the locking position to the release position.

Thus, the essential and special feature of the novel and inventive endoprosthesis for knee joint arthrodesis is that the femur portion and the tibia portion are not rigidly fixed relative to one another via the respectively involved coupling sections at an unalterable predefined angle, but rather here they have the possibility of pivoting. However, unlike genuine joint prostheses intended to replace the joint function of the natural joint, this possibility of pivoting is not freely available for reproducing a natural joint function. Instead, in the case of the endoprosthesis according to the invention, it is provided that said endoprosthesis locks in predefined pivot positions and thus produces and maintains a rigid and stiff connection between femur and tibia at a predefined angle. The locking element, which is held in a locking position by the retaining and return means, so that in a normal position, the endoprosthesis according to the invention is situated in a locked and stiffened position defined with respect to the angularity between the tibia and the femur, is provided for this purpose. However, it is precisely the locking element that may be released from the locking position with the aid of the release mechanism, and a different pivot angle between the tibia and femur may then be set. Because of the extensive deterioration in the area of the former knee joint, the patient will typically not perform a corresponding flexion or stretching to change the pivot angle on his or her own using the musculature of the leg in question. Instead, the patient will set the appropriate pivot angle externally, thus, for example, with the aid of his or her arms and hands, and then, by loosening the release mechanism, will ensure that the locking element, due to the holding and release mechanism, locks again in the pivot position now set, and thereby fixes and stiffens the tibia and femur at this flexion angle relative to one another.

The special feature of the release mechanism here is that it is to be operated outside of the leg. In particular, it is not necessary for any components of the endoprosthesis to be exposed and passed through the skin, but rather the affected patient is able to operate the release mechanism of the implant situated in the interior of the body, the endoprosthesis according to the invention, through the skin and the overlying tissue from the outside. In principle, an actuation switch or button, for example, would be applicable, which is disposed under the skin and, optionally, under additional tissue, and which the patient is able to actuate by pressing it, for example. Here, however, a design variant is preferred, in which the locking element includes a magnetic element as part of the release mechanism, to which a force may be applied with a magnet guided from the outside in the proximity of this magnetic element, by means of which the locking element may be displaced against the holding force from the locking position to the release position. With such a solution, the patient is able to unlock the endoprosthesis with the aid of a sufficiently powerful magnet guided by him, by moving this magnet near the knee thus bridged and, in this way, applying an appropriately strong magnetic force to the locking element through the skin and the underlying tissue, in order to move the locking element from the locking position to the release position.

The patient is able to calmly release, with the magnet, for example, the locking element inside the endoprosthesis through the soft tissue mantle, which then permits a movement of the knee joint. In this way, the patient is able to sit with a bent knee joint, for example, in an airplane or movie theater. He is also able to perform sexual activities with the affected knee in the flexed position. When riding a bicycle, the leg may swing concurrently as a passive leg if the patient is preoccupied with a possibility of continuous pivoting of the two parts, tibia portion and femur portion, of the endoprosthesis by corresponding continuous actuation of the locking element (i.e., holding the same in the release position).

According to another advantageous refinement of the invention, it is provided that one of the coupling sections in the endoprosthesis, the coupling section on the femur side or the coupling section on the tibia side, includes a hollow cylindrical section, circular in cross section, sealed at both end faces, the cylinder longitudinal axis of which is oriented along the prosthesis pivot axis. In this design of the endoprosthesis according to the invention, the other coupling section, the coupling section on the tibia side or the coupling section on the femur side, also includes a chamfered bearing section extending parallel to the prosthesis pivot axis for rotatable mounting of the hollow cylindrical section about the longitudinal axis of the cylinder, as well as a stop wall extending transversely to the prosthesis pivot axis, the stop wall forming a stop on the end face for the hollow cylindrical section. In addition, at least two receiving holes oriented in parallel to the prosthesis pivot axis are provided in this design variant at different positions in the stop wall, and the locking element comprises a piston plate disposed in an interior space of the hollow cylinder and displaceable in the longitudinal direction of the cylinder, on which at least one locking pin is eccentrically disposed, extending in the longitudinal direction of the cylinder projecting from said piston plate in the direction of the stop wall. The free end of this locking pin penetrates an opening in the end face of the hollow cylinder section facing the stop wall and, in a relative pivot position of the two coupling sections, in which it rests flush with one of the receiving holes in the stop wall, is able to extend into or retract from said opening by a movement of the piston plate in the longitudinal direction of the cylinder.

This design creates a particularly simple possibility of relative movement limited to the prosthesis pivot axis, for which a safe and reliable locking capability is given in predefined pivot positions with the aid of the locking pin, which is able to extend into corresponding receiving holes of the stop wall.

In order, on the one hand, to ensure a particularly safe and fixed locking of the two elements, tibia portion and femur portion, in a predefined pivot position relative to one another and, on the other hand, to also be able to select multiple pivot positions, multiple, in particular, four uniformly and eccentrically disposed locking pins extending in the longitudinal direction of the cylinder may be fixed on the piston plate, as is provided in an advantageous refinement of the invention, wherein these correspondingly positioned openings penetrate the end face of the hollow cylindrical section facing the stop wall, and wherein receiving holes are provided in the stop wall in a number corresponding to the number of locking pins and in an arrangement corresponding to the arrangement or array of the locking pins. This therefore creates a locking effectuated by multiple locking pins and is therefore particularly strong and stable, as well as durable, which also withstands the corresponding load of the patient's body weight, for example, when walking with the leg stiffened in the extended position, without running the risk of, for example, unlocking and resulting in an unintended buckling of the leg in the area of the knee.

If, with the aforementioned solution that includes the piston plate, the release mechanism as described above is also implemented by the magnetic element connected to the locking element, as provided in an advantageous refinement of the invention, the piston plate may then include the magnetic element or be formed altogether by the magnetic element.

In order to guide the piston plate in the interior of the hollow cylinder in a non-rotational manner, said piston plate, according to a possible refinement of the invention, may advantageously include at least one recess projecting inward from its edge, which interacts with a rib formed on one of the walls delimiting the interior space of the hollow cylindrical section, which projects into the interior space and extends in the longitudinal direction of the cylinder, and the cross section of which is adapted to the shape of the recess, in order to thereby maintain a rotationally-resistant and also tilt-resistant guidance of the piston plate.

According to another advantageous refinement of the endoprosthesis according to the invention, the free end of the at least one locking pin may be formed from a magnetizable or from a magnetic material, and a holding magnet, which forms the holding and return means, may be disposed in each of the receiving holes. This retaining magnet exerts a magnetic pull on the locking pin disposed opposite thereof, so that the locking pin, when it is situated in a position flush with the receiving hole, is drawn into this receiving hole into the locking position, in which it safely locks the endoprosthesis in a predefined pivot position.

As is provided by a particular refinement of the invention, the hollow cylindrical section may be advantageously formed on the coupling section on the femur side, the bearing section being disposed on the coupling section on the tibia side.

The two coupling sections in the endoprosthesis according to the invention are, in particular, pivotably but otherwise not displaceably connected relative to one another. According to one advantageous refinement of the invention, a pivot- and threaded bolt guided along the prosthesis pivot axis connecting the two coupling sections may be used for such connection. A pivot- and threaded bolt is understood in terms of this invention to mean a threaded bolt which may be secured by screwing an outer thread formed on its shaft onto a corresponding inner thread in a bolt slot, but which also has a smooth surface shaft section, which then forms a rotational axis or a pivot bearing in relation to a smooth-surface section of an opening through which the pin is guided.

In order to ensure, in the case of the endoprosthesis according to the invention, that flexion angles between the femur and the tibia cannot, for example, be set, which make no sense anatomically, but rather could represent a danger to the patient, pivot angle limiting structures may be advantageously present on the interacting coupling sections, which limit a relative pivoting of the tibia portion and the femur portion with respect to a predefined pivot angle.

Finally, according to advantageous refinements of the invention, the femur attachment structure may be a femur shaft and the tibia attachment structure may be a tibia shaft. Such shaft attachments are sufficiently known and have proven to be especially suitable for securing on the distal femur end or on the proximal femur end by inserting these shaft structures in the medullary cavity of the respective long bone and securing them there, for example, by means of bone cement.

Further advantages and features of the endoprosthesis for knee joint arthrodesis according to the invention arise from the following description of a possible exemplary embodiment with reference to the appended drawings, in which.

An exemplary embodiment for an endoprosthesis for knee joint arthrodesis is depicted in the figures, the exemplary embodiment being described below for clarity and for explaining the invention in further detail. The figures in this case are to be understood as schematic representations, which show the essential elements of the exemplary embodiment and are in no way to be understood as complete design drawings.

Figure 1:
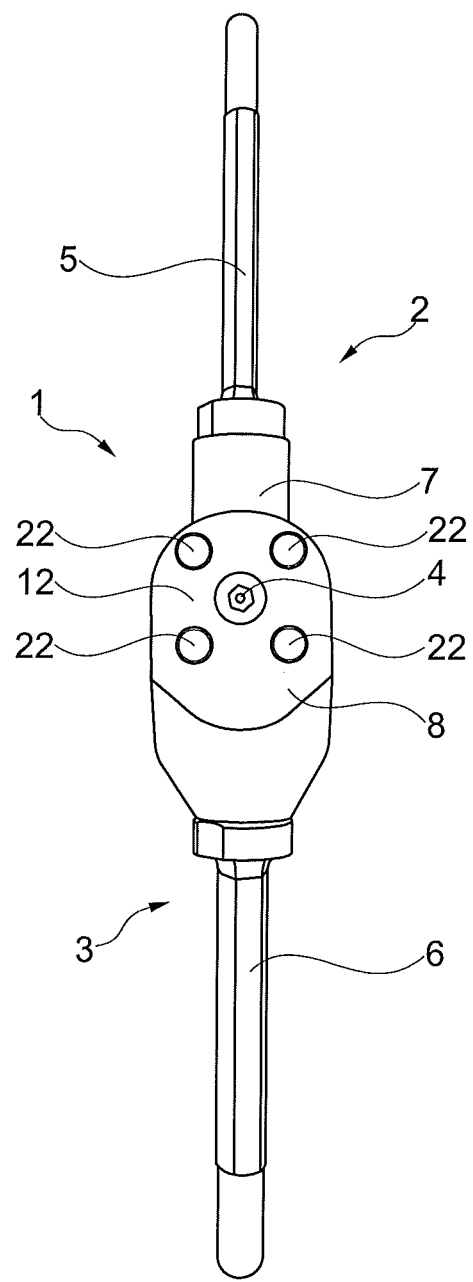
FIG. 1 shows an exemplary embodiment of an endoprosthesis for knee joint arthrodesis according to the invention locked in an extended position.
Figure 2:
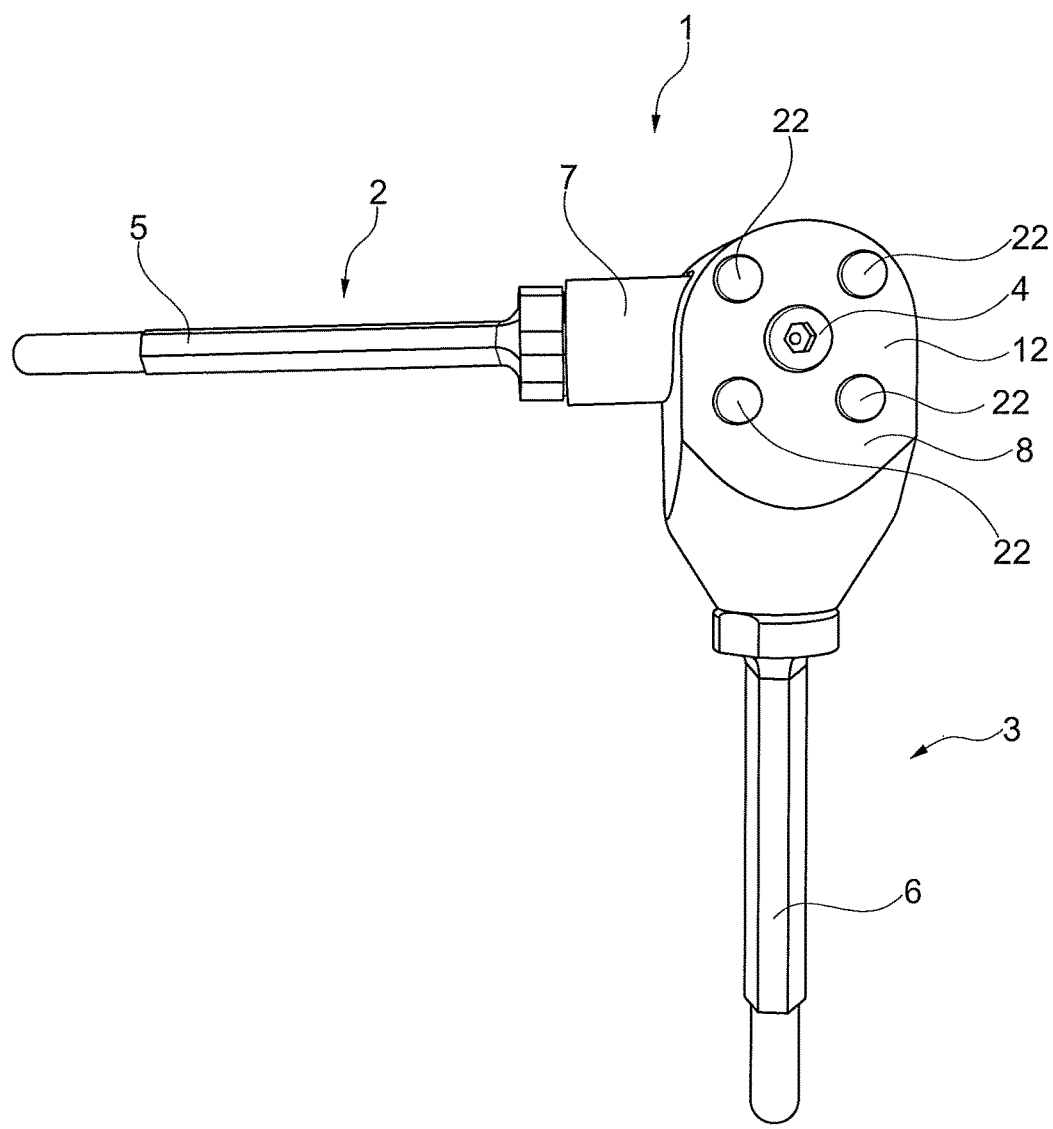
FIG. 2 shows the endoprosthesis according to FIG. 1, but brought into and locked in the flexed position.

The exemplary embodiment shown in the figures shows one possible design variant of an endoprosthesis according to the invention, which is universally identified in the figures with reference numeral 1. This endoprosthesis 1 has a femur portion 2 and a tibia portion 3 connected to one another with the aid of a pivot- and threaded bolt 4. In the endoprosthesis 1 according to the invention, the femur portion 2 and the tibia portion 3 are pivotable relative to one another about a prosthesis pivot axis, which extends along the longitudinal axis of the secured pivot and threaded bolt 4. In this way, the endoprosthesis 1 may, for example, be set in an extended position shown in FIG. 1 and fixed therein (more on this below), but alternatively also in a flexed position shown in FIG. 2.

A femur shaft 5, which is secured in a known manner in the medullary cavity of the distal femur end, typically cemented in place with bone cement, is mounted and secured to the femur portion 2 of the endoprosthesis, in order to securely connect the femur portion 2 to the femur of the patient. Similarly, a tibia shaft 6, which is introduced into the medullary cavity of the proximal tibia end and secured there, is secured to the tibia portion 3, in order to securely connect the tibia portion to the tibia of the patient. The femur portion also includes a coupling section 7 on the femur side; the tibia portion 3 is formed with a coupling section 8 on the tibia side. These two coupling sections 7, 8 are connected to one another by means of the pivot- and threaded bolt 4, and may be pivoted relative to one another about the prosthesis pivot axis.

In one implant situation, the prosthesis pivot axis extends essentially horizontally and from medial to lateral, and its position corresponds essentially to the main pivot axis of the natural knee joint (in this case without also being able to reproduce the pivotal movements about a vertical axis possible in the natural knee).

Figure 3:
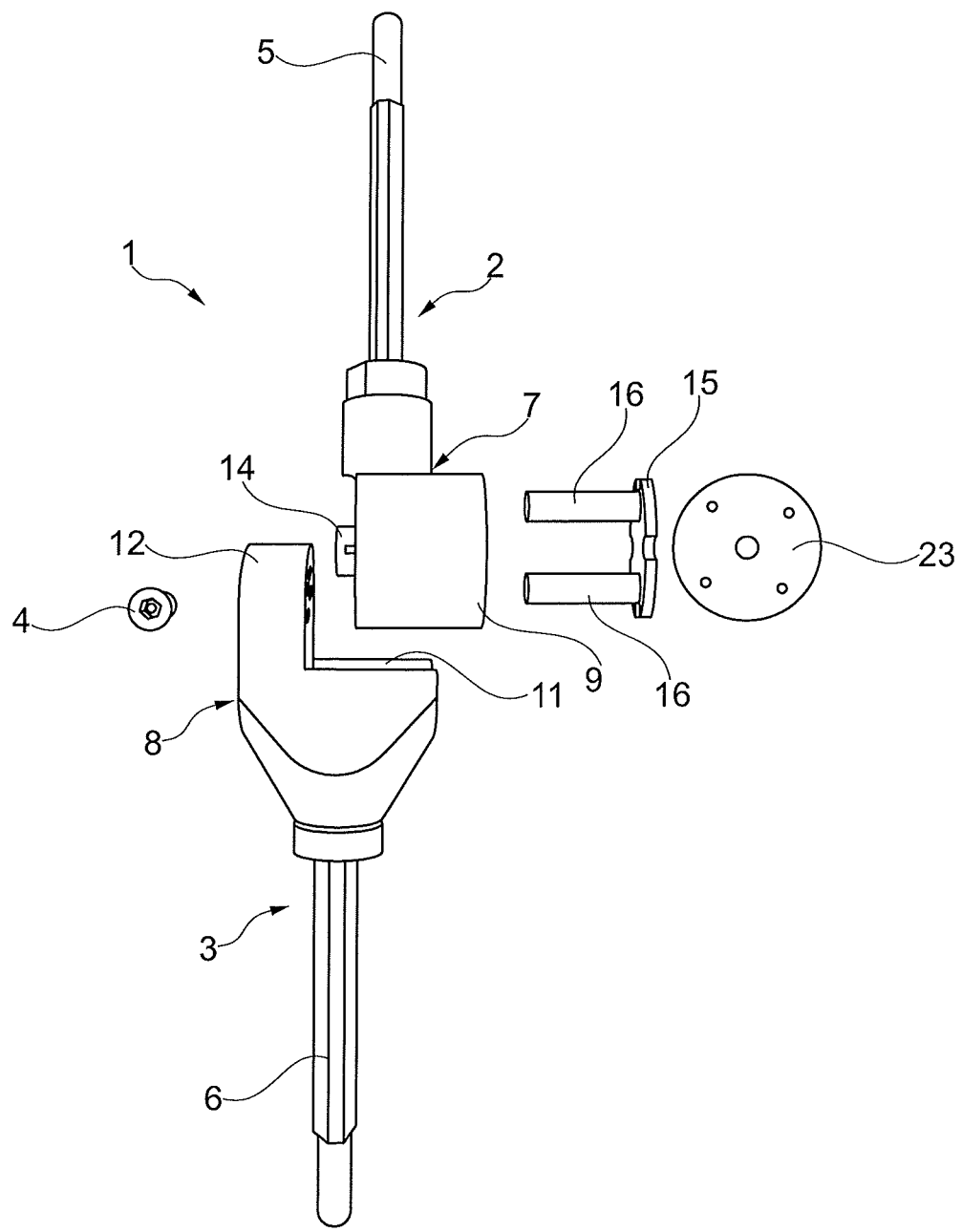
FIG. 3 shows the endoprosthesis from FIGS. 1 and 2 in an exploded view disassembled into the respective individual parts.
Figure 4:
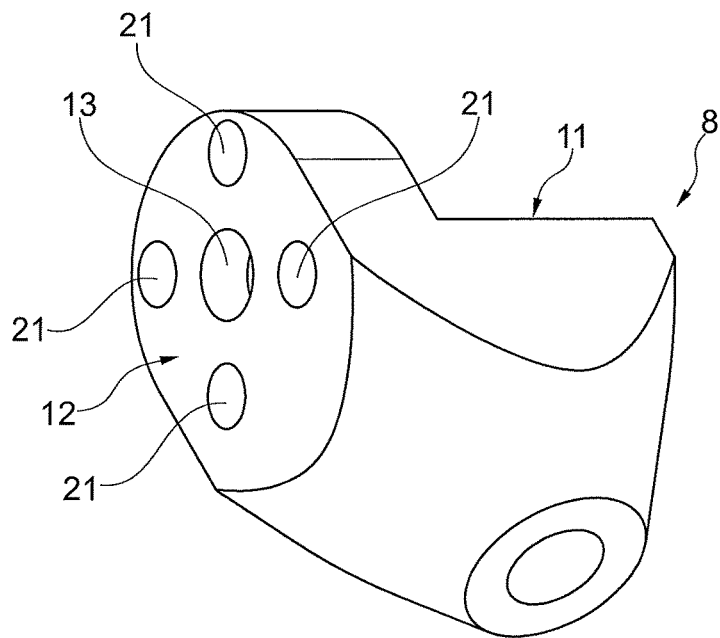
FIG. 4 shows a three-dimensional view of the coupling section of the endoprosthesis on the tibia side according to the exemplary embodiment.
Figure 5:
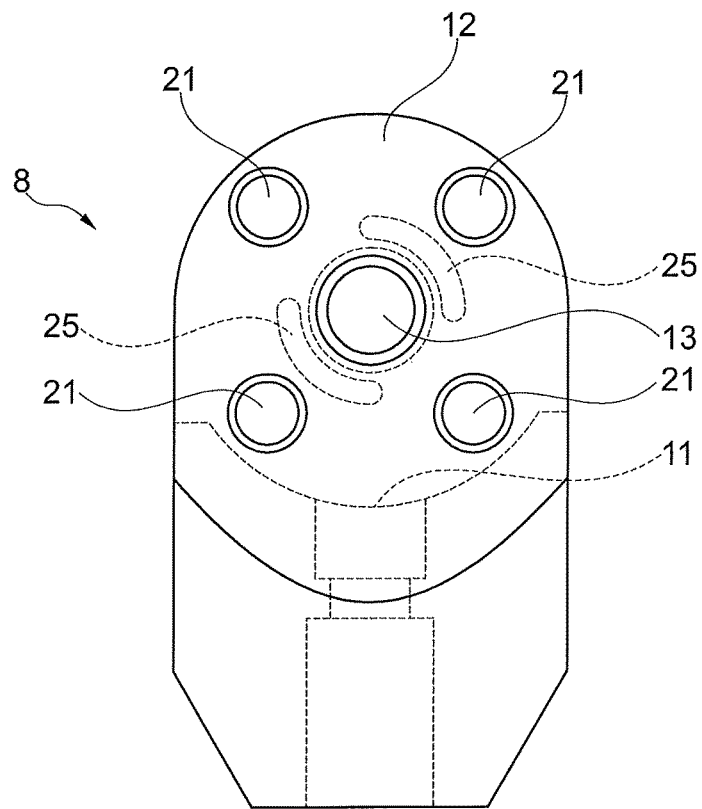
FIG. 5 shows a side view of the tibia section shown in FIG. 4 from the side in FIG. 4 depicted to the left.
Figure 7:
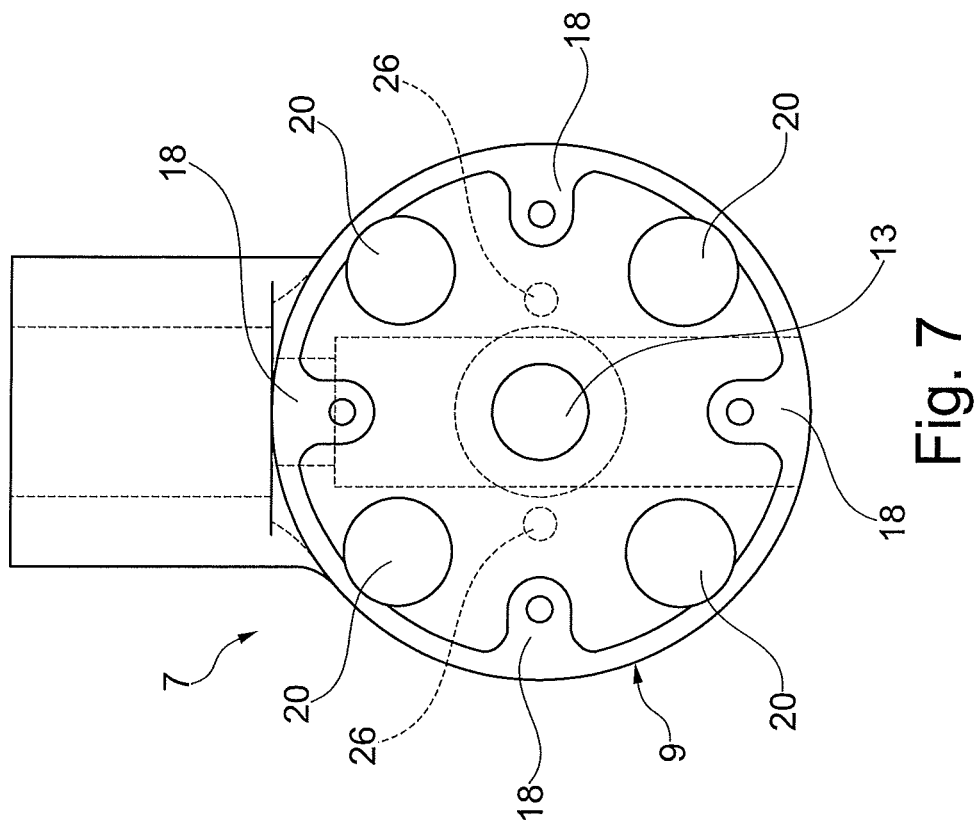
FIG. 7 shows a side view of the coupling section on the femur side from FIG. 6 from the side in FIG. 6 depicted to the left.
Figure 6:
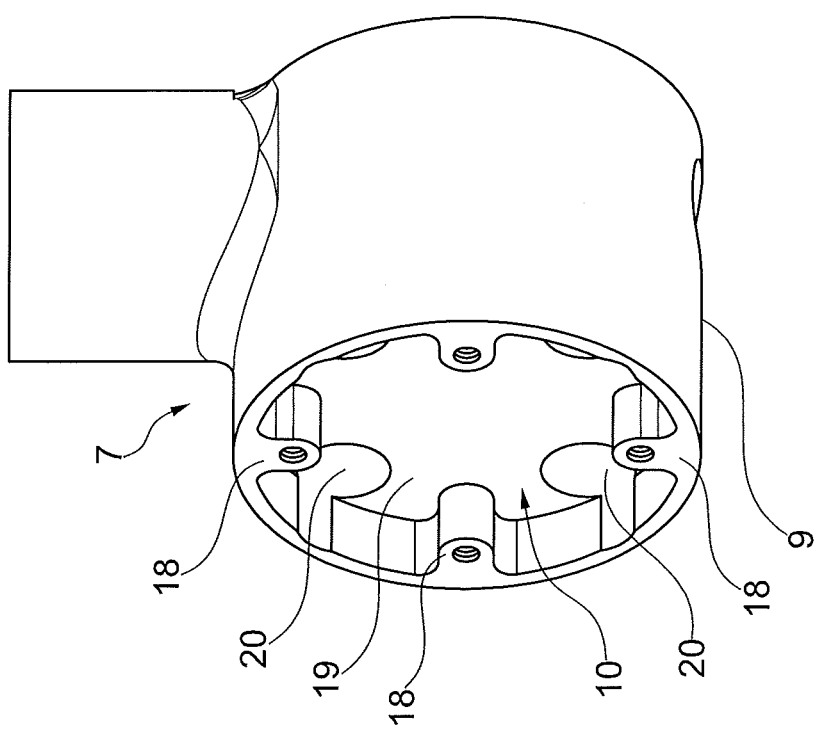
FIG. 6 shows a three-dimensional view of the coupling section of the endoprosthesis on the femur side according to the exemplary embodiment.

The exploded representation shown in FIG. 3 clearly shows that the coupling section 7 on the femur side includes a hollow cylindrical section 9, which has a circular diameter and includes an interior space 10 in its interior (cf. FIG. 6). This hollow cylindrical section 9 in the assembled state of the endoprosthesis 1, i.e., with the femur portion 2 and tibia portion 3 combined with the respective coupling sections 7, 8, is mounted in a chamfered bearing section 11 of the coupling section 8 on the tibia side, the chamfered bearing section 11 having a negative shape corresponding to the outer contour of the hollow cylindrical section 9. A stop wall 12 adjoins this bearing section 11 as an additional component of the coupling section 8 on the tibia side. A central feed-through hole 13 is located in said stop wall (cf. FIGS. 4 and 5), in which a center pin 14, which is molded to the end face of the hollow cylindrical section 9 facing the stop wall 12, is introduced from the side adjacent to the bearing section 11, and through which the pivot- and threaded bolt 4 is passed and screwed with an outer thread into an inner thread machined in a central hole in the center pin 14 to connect the two coupling sections 7, 8, in order to connect the femur portion 2 and the tibia portion 3 to one another in this way, but to also allow a pivoting about the prosthesis pivot axis.

Figure 8:
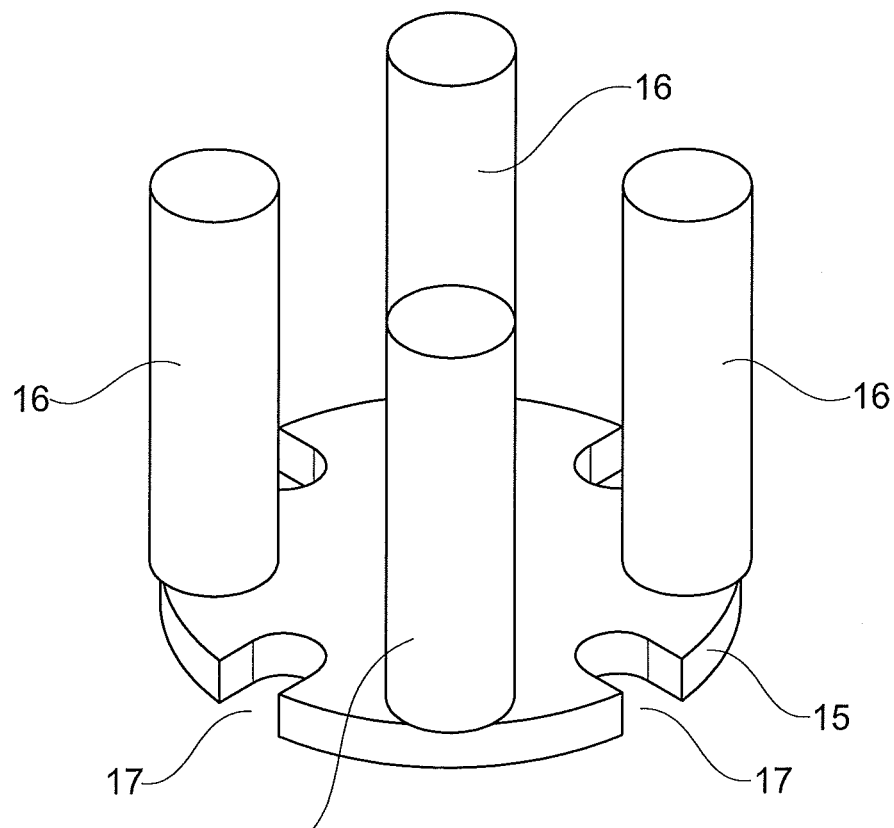
FIG. 8 shows a three-dimensional illustration of the locking element provided with four locking pins of the exemplary embodiment of the endoprosthesis according to the invention.

A locking element, which is formed from a piston plate 15 to which locking pins 16, oriented parallel in the longitudinal direction of the cylindrical section 9, are molded, is inserted into the interior space 10 of the hollow cylindrical section 9. As shown, in particular, in FIG. 8, a total of four locking pins 16 is eccentrically arranged on the piston plate 15, wherein the former are distributed in positions at an equal diameter and equidistant to one another. U-shaped recesses 17 (a total of four such recesses 17) are formed between the positions at which the locking pins of the piston plate 15 are molded, each directed from the outer side of the piston plate 15 toward the center thereof. These recesses encompass longitudinal ribs 18 extending in the longitudinal direction of the cylinder, which project inward into the interior space 10 of the hollow cylindrical section 9 in the assembled state, so that on the whole, the piston plate 15 is guided secured against rotation and tilting in the interior space 10 of the hollow cylindrical section 9.

The locking pins 16 penetrate openings 20 formed in the end wall 19 of the hollow cylindrical section 9. The piston plate 15 with the locking pins 16 molded thereon is disposed in the hollow space 10 of the hollow cylindrical section 9 and displaceable in the longitudinal direction of the cylinder. If, in this case, the piston plate 15 is forced against the end wall 19 and strikes the latter, the free ends of the locking pins 16 extend past the hollow cylindrical section 19 and, if the latter is positioned flush with the locking pins 16, engage in receiving openings 21, such that they lock the coupling section 7 on the femur side and the coupling section 8 on the tibia side in a pivot position relative to one another, and rigidly and fixedly lock the knee provided with the endoprosthesis 1 in an assumed pivot position (for example, an extended position according to FIG. 1 or a flexed position according to FIG. 2).

Finally, cylindrical permanent magnets 22 are introduced into and secured in the receiving openings 21 flush with the outer side of the stop wall 12 facing away from the bearing section 11. These permanent magnets, which may be, for example, neodymium N 48 magnets, exert a magnetic pull on the free ends of the locking pins 16 and, in a normal position, force them into the receiving holes 21, thus holding them in a locking position.

The hollow cylindrical section 9 is sealed on the end face facing away from the stop wall 12 with a cover plate 23 visible in FIG. 3, which is secured to the hollow cylindrical section 9 by means of four screws, which are screwed into corresponding threaded holes in the exposed end faces of the longitudinal ribs 18. In addition, this cover plate 23 forms a second stop for the piston plate 15, which is able to move back and forth in the interior space 10 with a corresponding stroke between the end wall 19 and the cover plate 23 in the direction of the longitudinal axis of the cylinder, and thus also in the direction of the prosthesis pivot axis.

Figure 9:
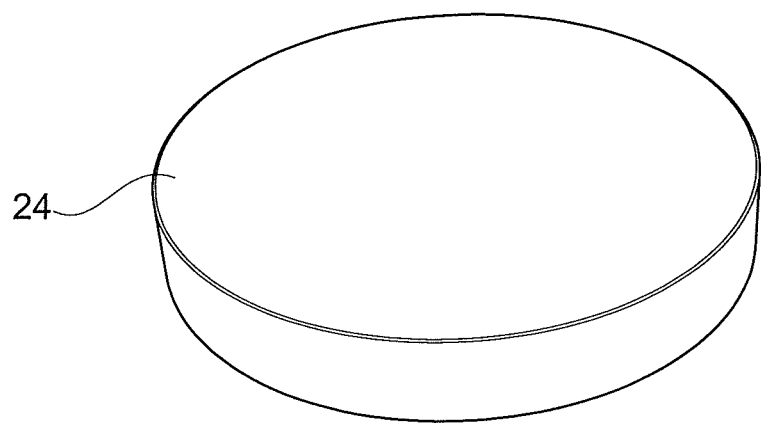
FIG. 9 shows a magnet for unlocking the locking element from outside the affected leg of a patient provided with the endoprosthesis according to the exemplary embodiment.

In order to then move the locking element in the form of the piston plate 15 with the locking pins 16 molded thereon from its locking position, in which the free ends of the locking pins 16 engage in the receiving openings 21 and are held there by the permanent magnets 22, into a release position, in which the free ends of the locking pins 16 are withdrawn completely from the receiving openings 21, a permanent magnet, for example, a neodymium N 48 magnet is used, as this is shown, for example, in FIG. 9 and is identified with the reference numeral 24. This permanent magnet 24 is advanced toward the knee from the outside provided with the endoprosthesis 1 according to the invention and has a sufficiently strong magnetic force to attract the magnetic or magnetizable piston plate 15 through skin and tissue and the cover plate 23. The permanent magnet 24 in this case has, in particular, a stronger magnetic force than the permanent magnets 22 disposed in the receiving openings 21, so that in spite of the holding force of the permanent magnets 22, the piston plate 15 with the locking pins 16 molded thereon, by overcoming this holding force, is pulled from the locking position into the release position, so that the endoprosthesis 1 and, therefore, the leg provided with it, may then be set in a different angular position. If the permanent magnet 24 is then withdrawn again from the immediate vicinity of the endoprosthesis 1, the permanent magnets 22 in the receiving openings 21 again pull the free ends of the locking pins 16 into the receiving openings 21, so that the free ends of the locking pins 16 extend into the receiving openings 21 when the latter are in flush alignment with the locking pins 16. The endoprosthesis 1, in turn, is thereby locked in another angular position.

Finally, it is also evident from the figures that structures for restricting the pivot angle are provided, by which the elements, femur portion 2 and tibia portion 3, may be pivoted relative to one another about the prosthesis pivot axis. These elements have opposing guide grooves 25 introduced on the inner side of the stop wall 12 facing the bearing section 11, each guided along an arc describing a maximum pivot angle, as well as guide pins 26 molded in diametrically opposed positions onto the outer end face of the hollow cylindrical section 9 facing the stop wall 12, which in the assembled state run from the coupling section 7 on the femur side with the coupling section 8 on the tibia side in the guide grooves 25 and, correspondingly, meet the stops restricting the pivot angle at the ends of these guide grooves.

From the foregoing description of an exemplary embodiment, it has become clear once again which particular advantages the endoprosthesis 1 for knee joint arthrodesis entails. The possibility provided here for the first time of being able to set and block an endoprosthesis for knee joint arthrodesis in different pivot positions, provides the affected patient with a significantly higher quality of life, since the patient is able, for example, when going to the movies or in an airplane, to articulate the affected leg by releasing the locking element and adjusting the pivot angle of the endoprosthesis 1 and to lock it again at this angle. With the patient permanently placing a permanent magnet, for example, with a cuff wrapped around the affected knee, in the area of the endoprosthesis in such a way that it, the permanent magnet, holds the piston plate 15 and with that, the locking pins 16 in the release position, in which the locking pins 16 are no longer situated in the receiving openings 21, it is also possible to create a passive pivotability in the knee area of the affected leg, so that, for example, with the foot of the affected leg appropriately fastened to a pedal, the affected patient is able ride a bicycle, wherein the leg provided with the endoprosthesis 1 swings concurrently in a passive manner, the propelling force being applied by the leg provided with a natural or a prosthetically replaced functioning knee joint.

LIST OF REFERENCE NUMERALS

1 Endoprosthesis
2 Femur portion
3 Tibia portion
4 Pivot- and threaded bolt
5 Femur shaft
6 Tibia shaft
7 Coupling section on the femur side
8 Coupling section on the tibia side
9 Hollow cylindrical section
10 Inner space
11 Bearing section
12 Stop wall
13 Feed-through hole
14 Center pin
15 Piston plate
16 Locking pin
17 Recess
18 Longitudinal rib
19 End wall
20 Opening
21 Receiving opening
22 Permanent magnet
23 Cover plate
24 Permanent magnet
25 Guide groove
26 Guide pin

The invention claimed is:

1. An endoprosthesis for knee joint arthrodesis comprising:
   a. a femur portion which includes a femur attachment structure for a fixed connection to a distal end of the femur;
   b. a tibia portion which includes a tibia attachment structure for a fixed connection to a proximal end of the tibia;
   c. a coupling section on a femur side formed on the femur portion;
   d. a coupling section on a tibia side formed on the tibia portion;
      wherein the coupling section on the femur side and the coupling section on the tibia side are pivotally connected relative to one another about a prosthesis pivot axis which extends in an installed position of the endoprosthesis, as a knee replacement, essentially horizontally from medial to lateral and, thus, corresponds in its position essentially to the position of the pivot axis of the natural knee;
   e. at least one locking element, which is moveable back and forth between a locking position in which the at least one locking element rigidly locks the coupling section on the femur side and the coupling section on the tibia side in a predefinable pivot position, and a release position in which a pivoting of the coupling section on the femur side and the coupling section on the tibia side relative to one another about the prosthesis pivot axis is enabled;
   f. a retaining and return means which forces the at least one locking element into the locking position with the aid of a holding force and holds the at least one locking element in said locking position;
      wherein the at least one locking element is adapted to cooperate with an external unlocking element by means of which the at least one locking element is displaceable against the holding force from the locking position to the release position; and
      wherein one of the coupling section on the femur side or the coupling section on the tibia side includes a hollow cylindrical section having a circular cross section sealed at both end faces; a cylinder longitudinal axis of which is oriented along the prosthesis pivot axis, and that the other of the coupling section on the tibia side or the coupling section on the femur side includes a chamfered bearing section extending parallel to the prosthesis pivot axis for rotatable mounting of the hollow cylindrical section about the cylinder longitudinal axis, and a stop wall extending transversely to the prosthesis pivot axis which forms a stop on an end face for the hollow cylindrical section, wherein at least two receiving holes oriented in parallel to the prosthesis pivot axis are provided at different positions in the stop wall, wherein the at least one locking element comprises a piston plate disposed in an interior space of the hollow cylindrical section and is displaceable in the longitudinal direction of the hollow cylindrical section and on which at least one locking pin projecting from said piston plate in the direction of the stop wall extending in the longitudinal direction of the hollow cylindrical section is eccentrically disposed, wherein a free end of the at least one penetrates an opening in the end face of the hollow cylindrical section facing the stop wall and, in a relative pivot position of the two coupling sections, in which the at least one locking pin rests flush with one of the receiving holes in the stop wall and is able to extend into or retract from said opening by a movement of the piston plate in the longitudinal direction of the hollow cylindrical section.

2. The endoprosthesis according to claim 1, wherein the external unlocking element comprises a magnet and wherein the at least one locking element has a magnetic element to which a force may be applied with the magnet of the external unlocking element moved into proximity with this magnetic element and by means of which the at least one locking element is displaceable against the holding force from the locking position to the release position.

3. The endoprosthesis according to claim 2, wherein the piston plate includes or forms the magnetic element.

4. The endoprosthesis according to claim 1, wherein multiple uniformly and eccentrically disposed locking pins extending in the longitudinal direction of the cylinder are fixed on the piston plate and correspondingly positioned openings penetrate the end face of the hollow cylindrical section facing the stop wall, and the receiving holes are provided in the stop wall in a number corresponding to number of locking pins and in an arrangement corresponding to the arrangement of the locking pins.

5. The endoprosthesis according to claim 4, wherein four uniformly and eccentrically disposed locking pins extend in the longitudinal direction of the hollow cylindrical section and are fixed on the piston plate.

6. The endoprosthesis according to claim 1 wherein the piston plate includes at least one recess projecting inward from an edge thereof, and that a rib adapted in cross section to the shape of the recess and projecting into the interior space and extending in the longitudinal direction of the hollow cylindrical section, is provided on a wall delimiting the interior space of the hollow cylindrical section, which rib engages in the recess for a rotationally-resistant and tilt-resistant guidance of the piston plate.

7. The endoprosthesis according to claim 1 wherein at least the free end of the locking pin is formed from a magnetizable or from a magnetic material and that a retaining magnet which forms the retaining and return means, is disposed in each of the receiving holes.

8. The endoprosthesis according to claim 1 wherein the hollow cylindrical section is disposed on the coupling section on the femur side and wherein the bearing section is disposed on the coupling section on the tibia side.

9. The endoprosthesis according to claim 1, wherein the coupling sections on the femur side and on the tibia side are rotationally connected relative to one another about the prosthesis pivot axis by means of a pivot and a threaded bolt guided along the prosthesis pivot axis.

10. The endoprosthesis according to claim 9, further comprising pivot angle limiting structures on the interacting coupling sections, which limit a relative pivoting of the tibia portion and the femur portion with respect to a predefined pivot angle.

11. The endoprosthesis according to claim 1, wherein the femur attachment structure is a femur shaft.

12. The endoprosthesis according claim 1, wherein the tibia attachment structure is a tibia shaft.

* * * * *

UNITED STATES PATENT AND TRADEMARK OFFICE
CERTIFICATE OF CORRECTION

| | |
|---|---|
| PATENT NO. | : 9,827,105 B2 |
| APPLICATION NO. | : 15/044524 |
| DATED | : November 28, 2017 |
| INVENTOR(S) | : Jens Sass et al. |

It is certified that error appears in the above-identified patent and that said Letters Patent is hereby corrected as shown below:

In the Claims

Column 11, Line 7 (Claim 1) "free end of the at least one penetrates" should be changed to --free end of the at least one locking pin penetrates--.

Signed and Sealed this
Twentieth Day of February, 2018

Andrei Iancu
*Director of the United States Patent and Trademark Office*